US00PP22690P2

(12) United States Plant Patent
Horvath

(10) Patent No.: US PP22,690 P2
(45) Date of Patent: Apr. 24, 2012

(54) *SEDUM* PLANT NAMED 'PLUM PERFECTION'

(50) Latin Name: ***Sedum* hybrid**
Varietal Denomination: Plum Perfection

(76) Inventor: Brent Horvath, Fontana, WI (US)

( * ) Notice: Subject to any disclaimer, the term of this patent is extended or adjusted under 35 U.S.C. 154(b) by 0 days.

(21) Appl. No.: 12/925,779

(22) Filed: Nov. 1, 2010

(51) Int. Cl.
*A01H 5/00* (2006.01)

(52) U.S. Cl. ..... Plt./479

(58) Field of Classification Search ..... Plt./479
See application file for complete search history.

*Primary Examiner* — Annette Para

(57) ABSTRACT

A new, distinct *Sedum* plant as shown and described, characterized by plum colored foliage, bicolor pink flowers and a larger height compared to the seed parent.

2 Drawing Sheets

Latin name: *Sedum* hybrid
Cultivar name: 'Plum Perfection'

BACKGROUND OF THE INVENTION

The present invention relates to a new and distinct hybrid of *Sedum* plant named 'Plum Perfection' characterized by plum colored foliage, bicolor pink flowers and a larger height compared to the seed parent. The new *Sedum* was raised as a seedling from open pollinated seed sown as an unknown *Sedum tatranowii*, not patented, in Hebron, Ill. in 2005. The selection of the new plant was due to its' plum colored foliage, bicolor pink flowers and a taller height compared to the seed parent. Initial asexual reproduction has taken place at a nursery in Hebron, Ill. since 2006 by means of division, and vegetative cuttings. The new *Sedum* has shown to be stable and identical in reproduction to the parent after rooting over 1200 plants from 2006 to 2010.

SUMMARY OF THE INVENTION

The new *Sedum* plant named 'Plum Perfection' characterized by plum colored foliage, bicolor pink flowers and a larger height compared to the seed parent have been observed to be unique and stable.

Plants of the new *Sedum* can be compared to plants of *Sedum* hybrid 'Bertram Anderson' not patented. 1. The new Sedum has smaller foliage measuring 25 mm long and 12-13 mm wide while *Sedum* hybrid 'Bertram Anderson' has larger foliage measuring 30-35 mm long and 17-19 mm wide. 2. The new *Sedum* plant has a mounding dome shaped habit while *Sedum* hybrid 'Bertram Anderson' has a semi-erect habit. 3. The new *Sedum* has bicolor pink flowers while *Sedum* hybrid 'Bertram Anderson' is deeper pink, almost carmine.

Plants of the new *Sedum* can also be compared to the seed parent plant *Sedum tatranowii*, not patented. 1. The new *Sedum* is a hybrid and does not produce seed while the seed parent plant is fertile and produces viable seed. 2. The new *Sedum* has a mature size of 25 cm high and 40-45 cm wide while the seed parent has a mature size of 12 cm high and 30 cm wide. 3. The new *Sedum* has larger foliage measuring on average up to 12-13 mm in width by 25 mm in length while the seed parent has foliage measuring 6 mm in width by 20 mm in length. 4. The new *Sedum* has a stem thickness of 4 mm while the seed parent has stem thickness of 2 mm.

DESCRIPTION OF PHOTOGRAPHS

Figure 1:
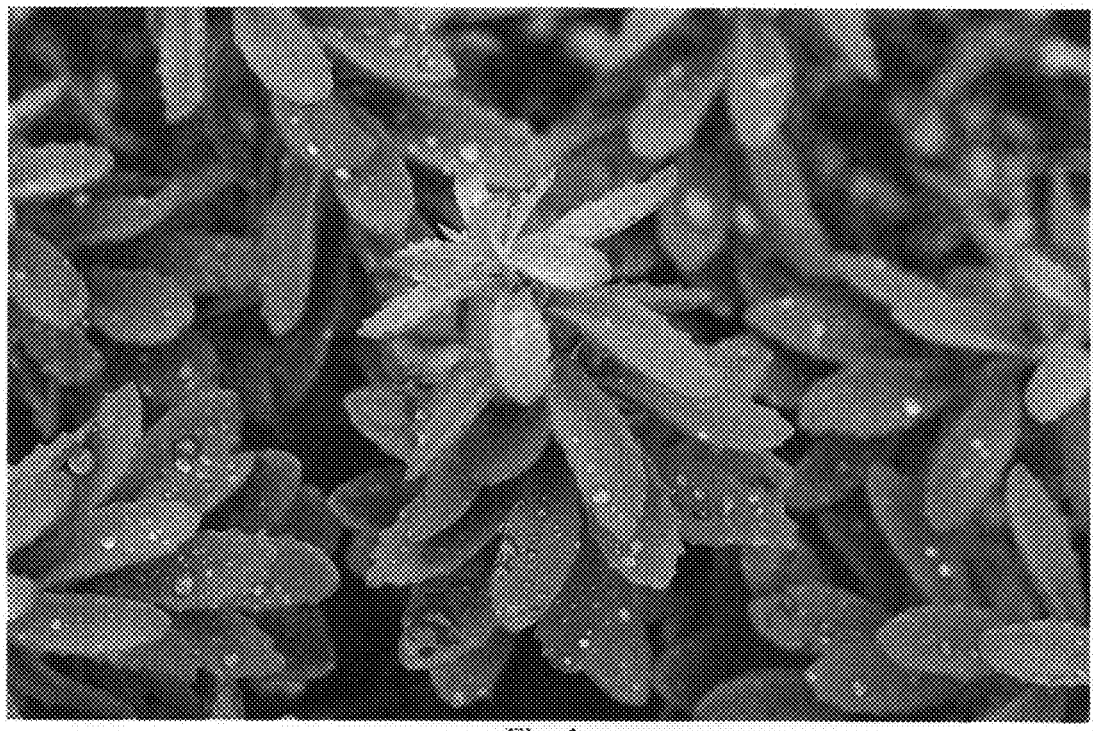
Figure 2:
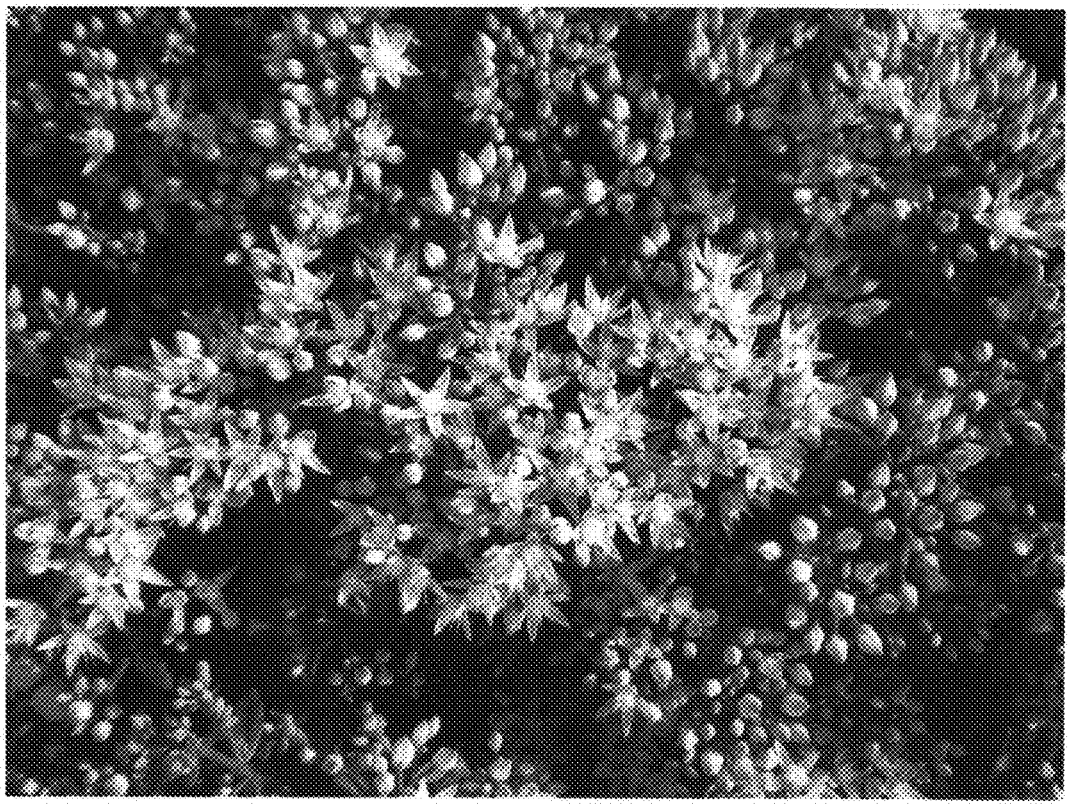
Figure 3:
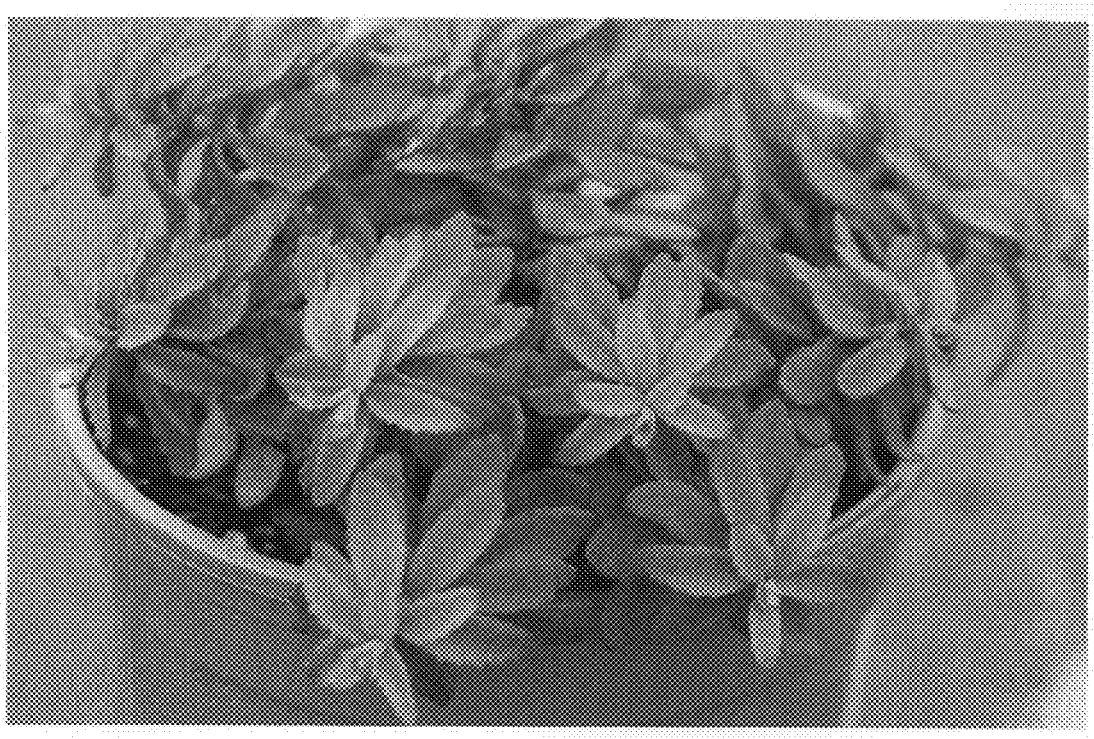
Figure 4:
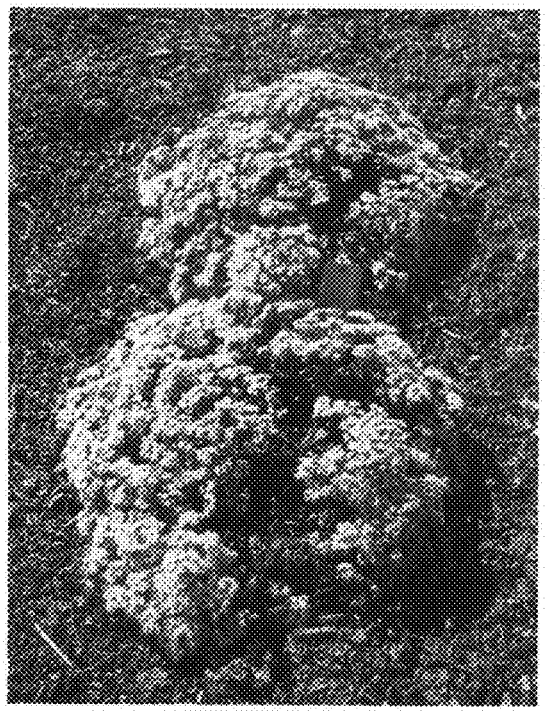

Plants pictured in the drawing were grown for two years.
FIG. 1. Close up of the foliage.
FIG. 2. Close up of the flower.
FIG. 3. A single plant in May.
FIG. 4. Two blooming plants in September

DETAILED BOTANICAL DESCRIPTION

In the following description, color references are made to The Royal Horticultural Society Colour Chart (2001). Plants used for the description were grown for two years. Measurements and numerical values represent averages of typical plants.

Botanical classification: *Sedum* hybrid cultivar 'Plum Perfection'.

Parentage: Male or pollen unknown and female or seed an open pollinated, unknown *Sedum tatranowii.*

Propagation: Vegetative division and cutting propagation.

Plant description: Overall habit of the new *Sedum* is basal clumps, with upright stems topped by bicolor pink flowers in August and September.

*Plant height.*—Average 25 cm.
*Plant width.*—40-45 cm.
*Stem color.*—Base=N200A; Top of stem near flower=187A.
*Stem length.*—30 cm.
*Stem diameter.*—4 mm.

Foliage:

*Type.*—Deciduous.
*Shape.*—Oblanceolate.
*Petiole.*—None.
*Length.*—25 mm.
*Width.*—12-13 mm.
*Thickness.*—1-2 mm.
*Margin.*—Serrate.
*Texture.*—Smooth.
*Leaf arrangement.*—Alternate, crowded except at the base of the stems.
*Leaf venation pattern.*—None noticed.
*Leaf vein color.*—None noticed.

Leaf color evolves from grey green at the growth tip of the plant to a plum color below the tip.

*Adaxial leaf description at the tip.*—Between 137 B & C.

*Abaxial leaf description at the tip.*—138 B.

*Adaxial leaf description at the base.*—N 77.

*Abaxial leaf description at the base.*—191 B.

*Fall foliage color.*—None noticed.

Flower:

*Petal count.*—5.

*Petal shape.*—Lanceolate.

*Adaxial petal color.*—186 C with the tip being 186 B.

*Abaxial petal color.*—186 D with the tip being 186 B.

*Petal apex shape.*—Acuminate.

*Petal base.*—2-3 mm wide.

*Petal length.*—2 mm.

*Petal width.*—1 mm.

*Flower type.*—Panicle on basal flowering stems.

*Panicle color.*—As a whole is between 186 B and 186 C.

*Flower cluster size.*—6 cm across, 3-4 mm tall.

*Flower number.*—Approximately 100+ per stem.

*Bloom period and duration.*—Mid August to Mid September.

*Sepal size.*—1 mm across, 2 mm tall.

*Carpel color.*—N 155 C.

*Fertility.*—Sterile, mostly insignificant anthers, pollen not always present, stamens mostly insignificant, sometimes not present. 1-2 mm long×less than 1 mm wide.

*Blooming habit.*—Domed, terminal panicle on up to 25 cm stems.

*Scent.*—No scent noticed.

*Fruit.*—None.

Disease resistance: Resistance to diseases common to *Sedum* has not been observed on plants grown under nursery conditions.

I claim:

1. A new, distinct *Sedum* plant as shown and described, characterized by plum colored foliage, bicolor pink flowers and a larger height compared to the seed parent.

* * * * *